United States Patent [19]

Chu

[11] Patent Number: 4,743,229
[45] Date of Patent: May 10, 1988

[54] COLLAGEN/MINERAL MIXING DEVICE AND METHOD

[75] Inventor: George Chu, Sunnyvale, Calif.

[73] Assignee: Collagen Corporation, Palo Alto, Calif.

[21] Appl. No.: 912,985

[22] Filed: Sep. 29, 1986

[51] Int. Cl.⁴ .............................................. A61B 5/10
[52] U.S. Cl. ..................................... 604/82; 604/110; 604/84
[58] Field of Search .................................. 604/82–85, 604/110; 128/764–766

[56] References Cited

U.S. PATENT DOCUMENTS

| | | | |
|---|---|---|---|
| 2,621,145 | 12/1952 | Sano | 167/84 |
| 3,010,705 | 11/1961 | Brown | 604/82 |
| 3,318,774 | 5/1967 | Dingwall et al. | 167/74 |
| 3,443,261 | 5/1969 | Battista et al. | 3/1 |
| 3,735,900 | 5/1973 | Gores | 604/82 |
| 3,820,167 | 6/1974 | Sivash | 3/1 |
| 3,918,100 | 11/1975 | Shaw et al. | 3/1.9 |
| 3,919,723 | 11/1975 | Heimke et al. | 3/1.9 |
| 4,186,486 | 2/1980 | Gordon | 433/201 |
| 4,243,080 | 1/1981 | Choksi et al. | 141/2 |
| 4,254,768 | 3/1981 | Ty | 128/218 |
| 4,306,554 | 12/1981 | Schwartz et al. | 128/218 |
| 4,314,380 | 2/1982 | Miyata et al. | 3/1.9 |
| 4,340,056 | 7/1982 | Erb | 128/272 |
| 4,359,049 | 11/1982 | Redl et al. | 128/218 |
| 4,378,211 | 3/1983 | Lococo | 433/36 |
| 4,424,057 | 1/1984 | House | 604/88 |
| 4,433,974 | 2/1984 | Bischof | 604/407 |
| 4,464,174 | 8/1984 | Ennis | 604/90 |
| 4,470,505 | 9/1984 | Korwin et al. | 206/219 |
| 4,496,344 | 1/1985 | Kamstra | 604/90 |
| 4,516,967 | 5/1985 | Kopfer | 604/87 |
| 4,529,403 | 7/1985 | Kamstra | 604/136 |
| 4,538,920 | 9/1985 | Drake | 366/177 |
| 4,540,410 | 9/1985 | Wood et al. | 604/56 |
| 4,551,135 | 11/1985 | Gorman et al. | 604/82 |

OTHER PUBLICATIONS

Hayashi, K., et al., *Arc Orthop Traumat Surg* 99: 265 (1980).

Eccleston, J. F., et al, *Analytical Biochemistry* 106: 73–77 (1980).

*Primary Examiner*—C. Fred Rosenbaum
*Assistant Examiner*—Gene B. Kartchner
*Attorney, Agent, or Firm*—Ciotti & Murashige, Irell & Manella

[57] ABSTRACT

A mixing device for preparing inductive and conductive bone repair compositions is disclosed, along with a method for using the device for preparing such compositions. The device provides a simple and rapid method of making a substantially uniform collagen/mineral bone implant preparation.

9 Claims, 1 Drawing Sheet

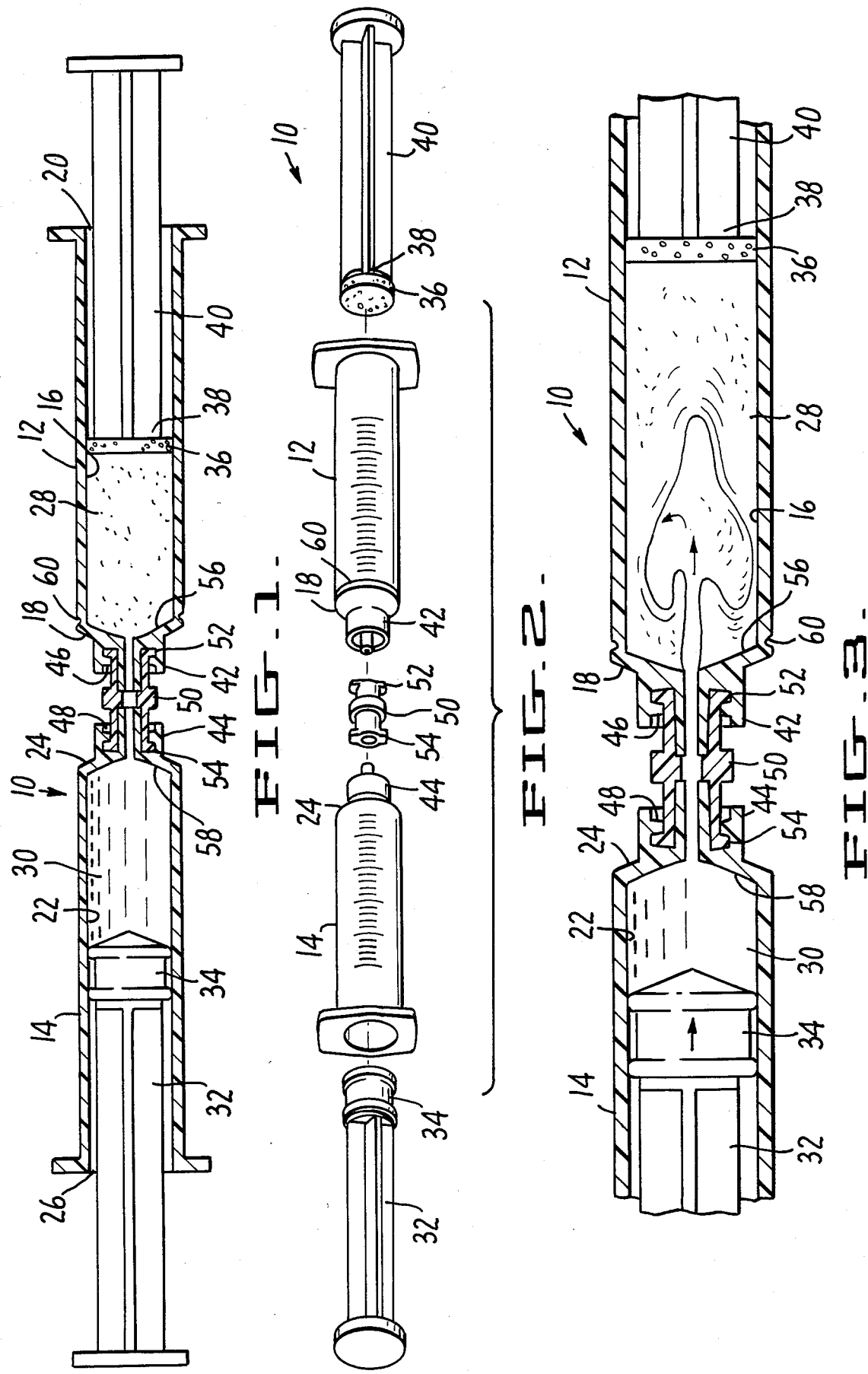

COLLAGEN/MINERAL MIXING DEVICE AND METHOD

FIELD OF THE INVENTION

This invention relates generally to preparation of bone repair compositions, and more specifically concerns a novel mixing device useful in preparing collagen/mineral bone repair compositions.

BACKGROUND OF THE INVENTION

The problem of repairing defective bone is clearly a continuing one. Until relatively recently, the only practical solution was to immobilize broken bones and rely on nature to effect regrowth of skeletal tissue into an injury. Only with the advent of the possibility of surgery has it become possible to actually implant bone substitutes, not only to replace injured or diseased bone structures, but also to repair congenital or degenerative defects in the skeletal structure.

A wide range of materials has since been utilized, and elaborate designs have been disclosed for replacements of entire portions of bones, e.g., for hip joints (U.S. Pat. No. 3,820,167) and teeth (U.S. Pat. No. 4,186,486). Materials employed have included metals such as titanium (EPO Pub. No. 0071242, published 9 Feb. 1983; U.S. Pat. No. 3,918,100), ceramics such as aluminum oxide (U.S. Pat. No. 3,919,723), shaped and treated bone (U.S. Pat. No. 3,318,774), and various bone preparations such as, for example, bone dust compacted into flexible mats (U.S. Pat. No. 2,621,145).

It has long been understood that skeletal structures have both inorganic and organic components. The inorganic component is a mineral, predominantly a form of calcium phosphate, hydroxyapatite. The organic component is chiefly composed of a single type of protein, collagen, which serves to impart a measure of resilience, thus preventing the structures from being unduly brittle. As skeletal tissue is alive, of course, additional metabolically active organic components must be included in the structure, and it is these bone cells and their active metabolites which are responsible for the naturally occurring healing and maintenance processes.

It has been determined that bone tissue repair occurs by one of two alternative mechanisms, or a combination of both. These mechanisms are referred to as conductive repair and inductive repair. In conductive repair, cells which are already committed to their character as bone cells (osteoprogenitor cells) move into the space of the defect from adjacent bone, and form bone directly. No special factors (other than non-specific nutrients) are required. In inductive repair, however, this process is preceded by conversion of previously uncommitted multipotential cells into osteoprogenitor cells which first form cartilage that calcifies and degenerates and is replaced by bone.

For either conductive or inductive repair, it is required that the living tissue or the host provide the ultimate skeletal structure. Thus the implant which mediates these processes serves not as a substitute for the defective or removed bone, but rather as a matrix support for active replacement of the missing tissue.

Accordingly, attempts have been made to devise implants for defective skeletal tissue or lesions in bones and teeth, which implants are intended precisely for this purpose. These implants do not attempt to mimic the composition of the missing bone, but rather serve as a structural support and guiding matrix for encroaching bone deposits derived from the adjacent fresh bone. These supports may provide only matrix support functions, i.e., mediate conductive repair, or they may, in addition, include factors which might mediate inductive repair such as by stimulating the differentiation of uncommitted cells to osteoprogenitor cells by providing what are currently known as "osteogenesis factors" (OF) or "bone morphogenic proteins" (BMP).

Because collagen is already a familiar material to the metabolically viable cells associated with bone growth, attempts have been made to use implants which are composed predominantly of collagen for both inductive and conductive repair.

Since the major components of bone from a quantitative standpoint are collagen and ceramic, various reconstituted implant compositions have been prepared using mixtures of ceramic materials and collagen. See, for example, U.S. Pat. No. 3,443,261; Hayashi, K., et al., *Arc Orthop Traumat Surg* 99:265 (1980); and U.S. Pat. No. 4,314,380.

In many collagen bone repair preparations it is thus necessary to initially mix a collagen dispersion or solution with a ceramic or mineral material. Additional factors as outlined above may be added to effect inductive rather than solely conductive repair.

Known mixing procedures, however, are not completely satisfactory. Typically a collagen dispersion is mixed with particulate ceramic material in a dish or other suitable container using an implement such as a spatula, rod, or the like. The process is frequently messy and time-consuming and, further, can result in problematic non-uniformity of the resulting paste. Thus, it is desirable to provide a mixing device which obviates these problems.

Several syringe-type mixing devices are known in the art. U.S. Pat. Nos. 4,254,768 to Ty and 4,538,920 to Drake each show a multiple barrel syringe device in which two materials are mixed just prior to injection. Similarly, U.S. Pat. No. 4,424,057 to House shows a "wet-dry" syringe which upon injection dissolves a solid component in a liquid component contained in a separate, internal vial. U.S. Pat. No. 4,496,344 to Kamstra shows a compartmental syringe in which two fluids are mixed upon injection. While several of these prior syringe-type mixing devices disclose dissolution of a solid in a fluid just prior to or upon injection, none shows a method for mixing a fluid or semi-fluid with a particulate solid in order to form a paste, nor is the specific preparation of bone repair compositions suggested.

SUMMARY OF THE INVENTION

Accordingly, it is an object of the present invention to provide a rapid mixing device for preparing collagen/mineral bone repair compositions.

It is another object of the present invention to provide a rapid mixing device, which device is structurally simple and thus easy and inexpensive to construct.

It is a further object of the present invention to provide a rapid mixing device which is especially useful in the precise admixture of small volumes of fluid, semifluid, and particulate solid.

It is still another object of the present invention to provide a method of making either inductive or conductive bone repair compositions using the novel rapid mixing device.

It is still a further object of the invention to provide a rapid mixing device which may be used to prepare bone repair compositions quickly and easily in a clinical setting.

Additinal objects, advantages and novel features of the invention will be set forth in part in the description which follows, and in part will become apparent to those skilled in the art on examination of the following, or may be learned by practice of the invention.

In one aspect of the invention, a method of preparing a collagen-mineral bone repair composition is provided, the method including use of a novel mixing device. The mixing device incorporates a first syringe containing reconstituted fibrillar atelopeptide collagen, a second syringe containing a particulate mineral material such as hydroxyapatite, and a locking connector means providing fluid communication between the two syringes. Upon injection of collagen into the first syringe containing particulate mineral material, a substantially uniform collagen-mineral paste is quickly and easily formed within that syringe. A means for allowing air trapped between the mineral particulates to escape is provided within the first syringe, and, optionally, a means for extruding the collagen-mineral mixture from the first syringe may be provided as well.

In an alternative embodiment of the invention, the method further includes the step of adding autogeneic bone marrow to the collagen-mineral mixture, yielding a biocompatible, inductive bone repair preparation.

BRIEF DESCRIPTION OF THE DRAWINGS

FIG. 1 is a front elevational view of the assembled mixing device.

FIG. 2 is an exploded, frontal view of the device illustrating the preferred means of connection between the two syringes.

FIG. 3 is an enlarged front elevational view of the central portion of the device illustrating admixture after injection.

DEFINITIONS

"Reconstituted" collagen refers to collagen which has been disassembled into individual triple helical molecules with or without their telopeptide extensions, brought into solution, and then regrouped into "fibrillar" form. In this form, the fribrils consist of long, thin collagen molecules staggered relative to one another by multiples about $\frac{1}{4}$ of their length. This results in a banded structure which can be further aggregated into fibers.

"Collagen dispersion" is a generic term referring to any collagen preparation in an aqueous medium where the collagen particle size is not specified, i.e., the preparation may be a solution, suspension or gel.

"Mineral" here refers to calcium phosphate mineral materials composed of calcium ($Ca^{+2}$) and phosphate ions, regardless of the microstructure, protonation status of the phosphate, or extent of hydration. Calcium phosphate mineral materials include a variety of forms, such as the commercially available forms of tricalcium phosphate (TCP), for example, Synthograft® tricalcium phosphate, or of hydroxyapatite (HA) such as Periograf®, Alveograf®, OrthoMatrix™ HA-1000®, or OrthoMatrix™ HA-500® hydroxyapatite particulate preparations. Any biocompatible calcium phosphate mineral may be used, but mixtures of TCP and HA are preferred.

"Marrow" here refers to autogeneic bone marrow preferably derived from the same individual who bears the defect to be repaired, or, if this is not possible, from an individual sufficiently closely related genetically that the materials derived from this individual are not immunogenic in the recipient. The methods of obtaining autogeneic bone marrow are standard in the art and do not form part of the invention.

DETAILED DESCRIPTION OF THE INVENTION

As briefly outlined above, the invention includes both a new rapid mixing device as well as a method for preparing bone repair compositions using the new device.

Turning now to the drawings, the mixing device is shown generally at 10. The device includes a first syringe 12 and a second syringe 14. First syringe 12 is provided with a hollow barrel 16 having a substantially closed end 18 and an open end 20. Similarly, second syringe 14 includes hollow barrel 22 having a substantially closed end 24 and an open end 26.

Upon using the device to prepare a collagenmineral bone repair composition, particulate mineral material 28 is inserted within first syringe 12, while a collagen composition 30 is inserted within second syringe 14. Collagen 30 is then injected into first syringe 12 through female Luer connector 50 by application of pressure on second plunger rod 32 directed longitudinally towards substantially closed end 24, rubber tip 34 of the plunger rod being maintained in direct contact with the collagen fluid.

During this admixture step, air trapped between the mineral particulates is allowed to escape by means of porous disk 36 at internal end 38 of first plunger rod 40. As collagen 30 is injected into first syringe 12, first plunger rod 40 is maintained firmly in place with disk 36 held in contact with the mineral material during the admixture process. Disk 36 of a hard plastic such as porous polyethylene is provided with relatively small pores (not illustrated) which must be smaller than mineral particulates 28 but large enough to allow air to pass through during injection. A suggested pore size is about $1\mu$.

The two syringes are connected by means of a relatively simple adapter system. First adapter 42 at substantially closed end 18 of first syringe 12 is joined to second adapter 44 at substantially closed end 24 of second syringe 14. These adapters are preferably male Luer connectors which may be provided with internal threads. During admixture, the adapters are joined by connector means 50 which is preferably a female Luer connector. End ridges 52 and 54 of the female Luer connector are adapted to fit within threads 46 and 48 of the male Luer connector. In an alternative embodiment, threads 46 and 48 may be replaced by an internal groove which provides a "snap"-type connection with female Luer connector 50. Thus, upon connection, the interiors 56 and 58 of first and second syringes are in fluid communication.

First syringe 12 is optionally provided with a means for extruding the collagen-mineral mixture as follows. Optional groove 60 adjacent substantially closed end of hollow barrel 16 enables the barrel to be easily cut or broken at that point after admixture, so that the mixture may then be extruded upon longitudinal application of pressure on first plunger rod 40.

Syringes 12 and 14 may be of virtually any diameter and volume; however, syringes that are narrower in diameter are preferred as they tend to provide more uniform mixture.

The collagen component to be used in the method of the present invention is important to the effectiveness of the bone repair preparation provided. Collagen suitable for use in the invention can be derived from a number of sources but is preferably in purified atelopeptide form to reduce immunogenicity. The collagen can be prepared from a variety of mammalian sources, most conveniently from bovine or porcine skins, and is treated with suitable proteolytic enzymes to remove the telopeptides. The preparation of such a biocompatible collagen is well known in the art and, indeed, commercial preparations of injectable collagen are available, such as Zyderm® II Collagen Implant, available from Collagen Corporation, Palo Alto, Calif. The collagen dispersion which is useful in the method of the invention typically has a collagen concentration of 35 mg/ml to 120 mg/ml, preferably 65 mg/ml to 85 mg/ml. Zyderm® II Collagen Implant has a concentration of 65 mg/ml.

Preferred minerals for use with the present invention include hydroxyapatite (HA) and hydroxyapatite mixed with tricalcium phosphate (HATCP). A preferred ratio of collagen dispersion to mineral is about 1:1 by weight, but ratios as high as about 4:1 are acceptable. Suitable particle sizes for the mineral component here vary. However, a preferred particle size ranges from about 250μ (60 mesh) to about 840μ (20 mesh).

The collagen-mineral paste prepared as described above is a conductive bone repair preparation which may be molded into a suitable implant. In an alternative embodiment of the invention, a suitable amount of bone marrow is added into the collagen-mineral paste using the mixing device of the invention, in order to provide an inductive preparation.

The inductive composition may be prepared in one of two ways. First, the marrow may be added into the collagen-mineral paste after injection of collagen into the particulate ceramic. This is done by placing a desired quantity of marrow into second syringe 14 and injecting that marrow into the first syringe containing the collagen-mineral mixture. Alternatively, the initial solution provided in the second syringe could be a mixture of collagen and marrow, which together are then injected into the mineral contained in first syringe 12.

Preferred inductive compositions which may be made using the method and device of the present invention include: from 1 to 10 g ceramic; from 1 cc to 10 cc collagen (65 mg/ml); and from 1 to 5 cc marrow. An exemplary composition is the following: 5 g ceramic; 5 cc collagen (65 mg/ml); and 2 cc marrow.

I claim:

1. A method of making a collagen-based bone repair preparation, comprising:
    providing a first and a second syringe each having a hollow barrel substantially closed at one end and open at a second end, said first syringe containing a quantity of a particulate mineral material and said second syringe containing a quantity of reconstituted fibrillar atelopeptide collagen, wherein said first syringe is provided with an air escape means comprising a plunger rod having a porous disk at said one end, said plunger rod being slidably insertable into said first syringe;
    aligning said first and second syringes so that said substantially closed ends of each of said syringes are proximate; and
    injecting said fibrillar collagen from said second syringe into said first syringe by applying longitudinal pressure on said plunger rod while maintaining said porous disk in contact with said fibrillar collagen, so that a relatively homogeneous collagen-mineral mixture is provided within said first syringe.

2. The method of claim 1, wherein said substantially closed ends of said first and second syringes are provided with adapters facilitating communication of fluid between the interiors of said first and second syringes.

3. The method of claim 2, wherein said adapters are joined during injection by a connector means.

4. The method of claim 1, further including the step of adding autogeneic bone marrow into said bone repair preparation.

5. The method of claim 4, wherein said marrow is added into said collagen-mineral mixture within said first syringe by injecting said marrow from said second syringe into said first syringe containing said mixture.

6. The method of claim 4, wherein said second syringe initially contains autogeneic bone marrow in addition to said reconstituted fibrillar atelopeptide collagen.

7. The method of claim 1, wherein said first syringe is provided with a circumferential groove adjacent said substantially closed end, and wherein said method further includes the step of extruding said collagen-mineral mixture from said first syringe by cutting said first syringe along said groove and applying longitudinal pressure towards said first end on said plunger rod.

8. A mixing device useful in preparing collagen-mineral bone repair compositions, comprising:
    a first and a second syringe, each having a hollow barrel substantially closed at one end and open at a second end, said first and second syringes provided with adapters at said substantially closed ends joined by a connecting means so that the interiors of said first and second syringes are in fluid communication, wherein said first syringe is provided with an air escape means comprising a plunger rod having a porous disk at said one end, said plunger rod being slidably insertable into said first syringe, and wherein said first syringe is further provided with an extruding means comprising a circumferential groove in said hollow barrel of said first syringe adjacent said substantially closed end.

9. The mixing device of claim 8, wherein said first syringe is provided with a quantity of a particulate mineral material and said second syringe is provided with a quantity of reconstituted fibrillar atelopeptide collagen.

* * * * *